United States Patent
Rudrapatna et al.

(10) Patent No.: US 12,204,007 B2
(45) Date of Patent: Jan. 21, 2025

(54) ESTIMATION OF $B_0$ INHOMOGENEITIES FOR IMPROVED ACQUISITION AND/OR RECONSTRUCTION OF MAGNETIC RESONANCE IMAGES

(71) Applicant: KONINKLIJKE PHILIPS N.V., Eindhoven (NL)

(72) Inventors: Umesh Suryanarayana Rudrapatna, Bangalore (IN); Jaladhar Neelavalli, Bengaluru (IN); Karthik Gopalakrishnan, Bangalore (IN); Suthambhara Nagaraj, Mysore (IN); Naveen Bajaj, Bangalore (IN); Rupesh Vakkachi Kandi, Kozhikode (IN)

(73) Assignee: Koninklijke Philips N.V., Eindhoven (NL)

( * ) Notice: Subject to any disclaimer, the term of this patent is extended or adjusted under 35 U.S.C. 154(b) by 8 days.

(21) Appl. No.: 18/008,193

(22) PCT Filed: Jun. 10, 2021

(86) PCT No.: PCT/EP2021/065586
§ 371 (c)(1),
(2) Date: Dec. 5, 2022

(87) PCT Pub. No.: WO2021/254861
PCT Pub. Date: Dec. 23, 2021

(65) Prior Publication Data
US 2023/0280429 A1   Sep. 7, 2023

(30) Foreign Application Priority Data

Jun. 15, 2020 (EP) .................................... 20179903

(51) Int. Cl.
*G01R 33/56* (2006.01)
*A61B 5/055* (2006.01)
(Continued)

(52) U.S. Cl.
CPC .......... *G01R 33/5608* (2013.01); *A61B 5/055* (2013.01); *G01R 33/3875* (2013.01);
(Continued)

(58) Field of Classification Search
CPC ............ G01R 33/5608; G01R 33/3875; G01R 33/4824; G01R 33/543; G01R 33/5611;
(Continued)

(56) References Cited

U.S. PATENT DOCUMENTS

2006/0220645 A1   10/2006   Zhang
2012/0268121 A1*  10/2012   Hernando .......... G01R 33/4828
                                                324/309
(Continued)

OTHER PUBLICATIONS

Shi et al "Template-Based Field Map Prediction for Rapid Whole Brain BO Shimming" Magnetic Reson. in Med. 80 p. 171-180 (2018).
(Continued)

*Primary Examiner* — G.M. A Hyder

(57) ABSTRACT

Disclosed herein is a medical system (100, 300, 500) comprising a memory (110) storing machine executable instructions (120) and a $B_0$ field estimation module (126); and a computational system (106). Execution of the machine executable instructions causes the computational system to receive (200) an initial magnetic resonance image (122) that comprises a magnitude component and is descriptive of a first region (326) of interest of a subject (118). Execution of the machine executable instructions further causes the computational system to perform at least one iteration of the following: receive (202) subsequent k-space data (124) descriptive of subsequent region of interest (328) of the subject; calculate (204) an estimated $B_0$ field mapping (128) for the subsequent region of interest from the initial magnetic resonance image by inputting the initial magnetic resonance image into the $B_0$ field estimation module; and
(Continued)

reconstruct (206) a corrected magnetic resonance image (130) from the subsequent k-space data and the estimated $B_0$ field mapping.

20 Claims, 10 Drawing Sheets

(51) Int. Cl.
G01R 33/3875 (2006.01)
G01R 33/48 (2006.01)
G01R 33/54 (2006.01)
G01R 33/561 (2006.01)
G01R 33/565 (2006.01)
G06N 3/02 (2006.01)

(52) U.S. Cl.
CPC ....... G01R 33/4824 (2013.01); G01R 33/543 (2013.01); G01R 33/5611 (2013.01); G01R 33/5616 (2013.01); G01R 33/56509 (2013.01); G01R 33/56518 (2013.01); G01R 33/56563 (2013.01); G06N 3/02 (2013.01)

(58) Field of Classification Search
CPC .......... G01R 33/5616; G01R 33/56509; G01R 33/56518; G01R 33/56563; G01R 33/4835; G01R 33/243; A61B 5/055; G06N 3/02; G06N 3/045; G06N 3/084; G06N 5/01; G06N 20/10; G06N 20/20
See application file for complete search history.

(56) References Cited

U.S. PATENT DOCUMENTS

| | | | |
|---|---|---|---|
| 2015/0355306 A1 | 12/2015 | Stemmer | |
| 2016/0131732 A1* | 5/2016 | Pfeuffer | G01R 33/56536 324/322 |
| 2016/0274205 A1 | 9/2016 | Stemmer | |
| 2020/0072931 A1 | 3/2020 | Zaiss et al. | |
| 2022/0179028 A1* | 6/2022 | Valvano | G06T 11/006 |
| 2022/0189081 A1* | 6/2022 | Daval-Frerot | G01R 33/5608 |

OTHER PUBLICATIONS

Alhamud et al "Real-Time Measurement and Correction of Both B0 Changes and Subject Motion in Diffusion Tensor Imaging Using a Double Volumetric Navigated (DvNav) Sequence" Neuroimge, vol. 126, Nov. 14, 2015 p. 60-71.

International Search Report and Written Opinion from PCT/EP2021/065586 mailed Sep. 6, 2021.

Liao et al "Referenceless Distortion Correction of Gradient Echo Echo Planar Imaging under Inhomogeneous Magnetic Fileds Based on a Deep Convolutional Neural Network" Computers in Biology and Medicine, 100 (2018) p. 230-238.

Boegle et al "Combining Prospective Motion Correction and Distortion Correction for EPI: Towards a Comprehensive Correction of Motion and Susceptibility-Induced Artifacts" Magn. Reson. Mater Phy. (2010) 23 p. 263-273.

Yarach et al "Correction of B0 Induced Geometric Distortion Variations in Prospective Motion Correction for 7T MRI" Magn. Reson. Mater Phy. (2016) 29 p. 319-332.

Cao et al "Simultaneous Segmentation and Relaxometry for MRI Through Multitask Learning" Department of Radiology Thesis.

Mueller et al "Diffusion MRI with b=1000 s/mm2 at TE<22 ms Using Single Shot Spiral Readout and Ultrastrong Gradients: Implications for Microstructure Imaging" ISMRM Annual Meeting May 11-16, 2019.

Andersson et al "An Integrated Approach to Correction for Off-Resonance Effects and Subject Movement in Diffusion MR Imaging" NeuroImage 125 (2016) p. 1063-1078.

Graham et al "Quantative Assessment of the Susceptibility Artefact and its Interaction with Motion in Diffusion MRI" PlosOne 12(10) Apr. 26, 2017.

Andreson et al "Modeling Geometric Deformations in EPI Time Series" NeuroImage 13 p. 903-919 (2001).

Anderson et al "An Integrated Approach to Correction of Off-Resonance Effects and Subject Movement in Diffusion MR Imaging" NeuroImage 125 (2016) p. 1063-1078.

Lange et al "Estimating Susceptibility-Induced Field Changes Directly from Difffusion MIR Images and Overcoming Associated Computational Bottlenecks through GPU Parallelisation" ISMRM 2018.

Sulikowska et al "Will Field Shifts due to Head Rotation Compromise Motion Correction" Proc. Intl. Mag. Reson. Med. 22 (2014) p. 885.

Rudrapanta et al "Can We Correct for Interactions Between Subject Motion and Gradient Nonlinearlity in Duffision MRI?" ISMRM 2018.

Bornert et al "Single Shot Diffusion Weighted Spiral Imaging in the Brain on a Clinical Scanner" ISMRM Annual Meeting May 11-16, 2019 (abstract).

Haskell et al "Deep Learning Field Map Estimation with Model-Based Image Reconstruction for Off Resonance Correction of Brain Images using Spiral Acquisition" 2020.

* cited by examiner

ESTIMATION OF $B_0$ INHOMOGENEITIES FOR IMPROVED ACQUISITION AND/OR RECONSTRUCTION OF MAGNETIC RESONANCE IMAGES

CROSS REFERENCE TO RELATED APPLICATIONS

This application is a U.S. national phase application of International Application No. PCT/EP2021/065586 filed Jun. 10, 2021, which claims the benefit of EP Application Ser. No. 20/179,903.8 filed on Jun. 15, 2020 and is incorporated herein by reference.

FIELD OF THE INVENTION

The invention relates to Magnetic Resonance Imaging, in particular to estimating $B_0$ inhomogeneities for improved image acquisition and/or reconstruction.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the $B_0$ magnetic field, the main magnetic field, or simply the $B_0$ field. Producing quality magnetic resonance images relies on correcting $B_0$ inhomogeneities in the $B_0$ field, for example using shimming, or compensating for $B_0$ inhomogeneities during reconstruction.

Shi et. al., "Template-Based Field Map Prediction for Rapid Whole Brain $B_0$ Shimming," Magnetic Resonance in Medicine 80:171-180 (2018) discloses a template-based method to determine the $B_0$ inhomogeneities caused by the presence of a human head in the $B_0$ field. The US-patent application US 2006/0220645 discloses $B_0$ maps generated specifically from actual acquisition (SSFP), with redundancy by way of phase increments.

SUMMARY OF THE INVENTION

The method provides for a medical system, a computer program, and a method in the independent claims. Embodiments are given in the dependent claims. For example the medical system is implemented as magnetic resonance imaging system, or MRI scanner. A patient to be examined may be positioned in the MRI scanner's examination zone.

As was mentioned above, the determination of inhomogeneities in the $B_0$ field is important for properly shimming the main magnet and also for the reconstruction of accurate magnetic resonance images. Typically, the $B_0$ field is measured by making magnetic resonance (MR) measurements at several different pulse times and noting a change in the phase. This provides accurate results, but it is time consuming. Another difficulty is that the subject being imaged may move after the $B_0$ map has been acquired.

Embodiment may provide for an improved means of determining a $B_0$ field mapping by using an initial magnetic resonance image to calculate an estimated $B_0$ field mapping for reconstructing subsequently acquired k-space data into a corrected magnetic resonance image. The initial magnetic resonance image could, for example be a so-called scout image or survey image. The scout image or survey image may have a first region of interest that could image a substantial portion of a subject's body or at least the portion of the subject's body within the imagining zone. There may be several advantages to this. Firstly, a survey image is normally acquired to align subsequent imaging procedures. It does not slow down the procedure. Another advantage may be that since the scout or survey image has a larger field of view than the subsequent images it takes into account a larger portion of the subject when determining how much the subject's body distorts the $B_0$ field. A detailed magnetic resonance image that images a volume within a subject's body may not provide accurate estimates of the $B_0$ field, because portions of the subject outside of the subsequent region of interest distort the $B_0$ field and may not be taken into account. An insight of the invention is that dominant contributions to the variability in $B_0$ inhomogeneity stem from different anatomical shapes and/or patient positioning inside the medical system's examination zone. Both these will be captured by the survey image. After the first scan (typically an initial survey scan), the actual diagnostic image acquired could differ. As long as there is significant overlap in the region-of-interest of the survey scan and the diagnostic image, a $B_0$-map may be predicted for the later images from the first magnitude image (Survey/Coil survey/Sense ref etc.). In particular, this is to address subject motion and breathing. The invention works with any magnitude image. It could even use a single SSFP scan. However, we intend to use survey and pre-scans which have much shorter acquisition and invariably needed in any session. Besides, the $B_0$-map generated according to the invention is widely useable, both for shimming (static and dynamic) and also in reconstruction of EPI/Spiral etc., and even in the presence of motion. The invention uses the "Shape information" in the magnitude image for predicting the $B_0$ distribution and does not require a pixel-by-pixel analysis. The invention can predict the $B_0$ distribution from a completely unrelated scan and thus is independent of the acquisition being performed. The invention uses structural information captured in the magnitude image and does not work on a pixel-by-pixel fit as known per se from the US-patent application US 2006/0220645. That is, the present invention makes use of information across-voxels for the prediction. The invention enables to predict the $B_0$ distribution even with motion or breathing across sequences. Data acquired after the first scan (subsequent image) could refer to a new position or change in shape of the object, e.g. a rotated head, inflated chest. Change in object position or shape leads to a change in $B_0$ distribution. Updated $B_0$ shim settings derived from the computed $B_0$-distribution refer to the update required because of these physiological changes.

In one aspect the invention provides for a medical system that comprises a memory storing machine-executable instructions and a computational system that is configured for controlling the medical system. In different examples the medical system could take different forms. In one example the medical system is a remote or cloud server that is used for performing the reconstruction of medical or magnetic resonance images. In another example the computational system is a workstation used by radiologists or other medical professionals to review or process medical image data such as magnetic resonance images. In yet another example the computational system is part of a medical system that includes a magnetic resonance imaging system. For example, the computational system could be the control system or part of a control system for controlling a magnetic resonance imaging system.

Execution of the machine-executable instructions causes the computational system to receive an initial magnetic resonance image descriptive of a first region of interest of a subject. The initial magnetic resonance image comprises a magnitude component. In some cases. The initial magnetic resonance image as described below is later used to calculate an estimated $B_0$ field mapping.

Execution of the machine-executable instructions further causes the computational system to perform the estimation of the $B_0$ field mapping. That is to receive subsequent k-space data descriptive of a subsequent different region of interest of the subject. The subsequent region of interest at least partially overlaps the first region of interest. Execution of the machine-executable instructions further causes the computational system to perform an iteration of the following at least once, which is to calculate an estimated $B_0$ field mapping for the subsequent region of interest from the initial magnetic resonance image using a $B_0$ field estimation module. Execution of the machine-executable instructions further causes the computational system to perform an iteration of the following at least once, which is to reconstruct a corrected magnetic resonance image from the subsequent k-space data and the estimated $B_0$ field mapping.

This embodiment may be advantageous because a prior magnetic resonance image, in this case the initial magnetic resonance image, may be used to generate an estimated $B_0$ field map which may be used for reconstructing the corrected magnetic resonance image. This may reduce or eliminate the need for a preliminary $B_0$ field map when performing a magnetic resonance imaging examination.

One instance in which this may be particularly advantageous is when the initial magnetic resonance image is a so-called survey or scout image. A survey or scout image is a preliminary image that is typically of lower resolution that is used to ascertain the location of particular anatomical regions of a subject. The use of a so-called survey or scout image may be beneficial because it may image a large region of the subject. The distribution of the body of the subject within a $B_0$ magnetic field causes distortions of the $B_0$ field.

The determination of the estimated $B_0$ field mapping may be performed in a variety of different ways. For example, the method may also include motion correction. For example, a sensor or camera could be used to measure the position of a subject over time and this data could be used to update the estimated $B_0$ field mapping from the initial magnetic resonance image. In other instances, the subsequent k-space data may be used to construct a preliminary magnetic resonance image that does not have motion or $B_0$ corrections. This may then be registered to the initial magnetic resonance image and used to determine motion parameters to then calculate a more accurate estimated $B_0$ field mapping.

The term estimated $B_0$ field mapping refers to data which is descriptive of the distortion of the $B_0$ field caused by a subject in the main magnet. The term estimated $B_0$ field mapping may therefore be interpreted in several different ways. $B_0$ residual map may for example be used to adjust the magnetic shims of a magnetic resonance imaging system to compensate for $B_0$ inhomogeneities caused by the subject. In another instance, the estimated $B_0$ field mapping could refer to the residual $B_0$ map (magnetic inhomogeneity that remains after shimming). In this case, the estimated $B_0$ field may be used to correct for the effects of $B_0$ magnetic field inhomogeneities during the reconstruction of highly sensitive techniques like echo planar imaging and imaging with non-Cartesian k-space trajectories like radial, spiral etc.

In another embodiment the medical system further comprises a magnetic resonance imaging system configured for acquiring k-space data from an imaging zone. The memory further contains first pulse sequence commands configured for acquiring initial k-space data from the first region of interest. The memory further contains a set of second pulse sequence commands each configured for acquiring the subsequent k-space data from the subsequent region of interest. Execution of the machine-executable instructions further causes the computational system to control the magnetic resonance imaging system with the first pulse sequence commands to acquire the initial k-space data.

Execution of the machine-executable instructions further causes the computational system to reconstruct the initial magnetic resonance image from the initial k-space data. Execution of the machine-executable instructions further causes the computational system to control the magnetic resonance imaging system with one of the set of second pulse sequence commands to acquire the subsequent k-space data for each iteration. This embodiment may be beneficial because it provides for a magnetic resonance imaging system that is able to provide for $B_0$ inhomogeneity reconstruction for multiple images from a single initial magnetic resonance image.

In another embodiment, the initial magnetic resonance image is a magnitude image. It is noted that the initial magnetic resonance image is a magnitude image and not a phase image.

In another embodiment the subsequent region of interest is within the first region of interest. The subsequent region of interest has a volume less than or equal to the first region of interest. The use of an image within a larger field of view or region of interest may enables a more accurate determination of the resulting estimated $B_0$ field mapping. For example, if an initial magnetic resonance image or a survey or scout image that image the whole head of a subject then the distortion in the $B_0$ or main magnetic field caused by the head can be accurately calculated. If the subsequent k-space data only images a small region of the head such as a portion of the brain, the $B_0$ field map from this subsequent region of interest may not give an accurate value as to the estimated $B_0$ field mapping.

In another embodiment, the subsequent region of interest has a volume greater than the first region of interest. The initial magnetic resonance image can in some cases be used to determine the estimated $B_0$ field mapping for a region that is larger than the first region of interest. For example, a template-based method could match the initial magnetic resonance image to a larger region to calculate the estimated $B_0$ field mapping for the subsequent region of interest. The same applies to artificial intelligence-based methods. Some magnetic resonance imaging protocols such as EPI can have significantly distorted images. The type of initial magnetic resonance image could be chosen to minimize distortion. For example, a convention gradient echo image could be acquired as the initial magnetic resonance image. Although the first region of interest is smaller than the subsequent region of interest its lack of distortion could lead to a more accurate estimated $B_0$ field mapping.

In another embodiment the magnetic resonance imaging system comprises a main magnet for generating a $B_0$ magnetic field in the imaging zone. The magnetic resonance imaging system further comprises an adjustable $B_0$ magnetic field shim configured for shimming the $B_0$ magnetic field in the imaging zone. Execution of the machine-executable instructions further causes the computational system to perform the following before each acquisition of the subsequent k-space data. This is to calculate updated $B_0$ shim settings configured to reduce $B_0$ inhomogeneity using the estimated $B_0$ field mapping. This may be beneficial because correcting the shim settings of the $B_0$ magnetic field increases the signal-to-noise in the k-space data. This provides for a better-quality magnetic resonance image once reconstruction is performed. This may have the effect of enabling a dynamic shimming process for improving the shimming of the $B_0$ magnetic field after every acquisition.

In another embodiment, execution of the machine-executable instructions further causes the computational system to calculate an initial $B_0$ field mapping for the subsequent region of interest directly from the initial magnetic resonance image. This for example may be useful for calculating the $B_0$ map before the subsequent k-space data is acquired the first time. This for example may be used for adjusting the magnetic shims for the main magnet.

In another embodiment the estimated $B_0$ field mapping is calculated at least partially using the updated $B_0$ shim settings. The adjustment of the $B_0$ magnetic field shim will change the $B_0$ magnetic field homogeneity. Therefore, it is advantageous to update the $B_0$ field mapping using the updated $B_0$ shim settings.

In another embodiment, execution of the machine-executable instructions further causes the computational system to perform the following steps during acquisition of the subsequent k-space data. One step performed during acquisition of the subsequent k-spaced data is to receive motion parameters descriptive of motion of the subject during or after the acquisition of the subsequent k-space data. Another step performed during acquisition of the subsequent k-spaced data is to calculate the estimated $B_0$ field at least partially using the motion parameters. The estimated $B_0$ field can then be used during image reconstruction.

In another embodiment, the medical system further comprises a motion sensor system configured for at least partially measuring the motion parameters. Execution of the machine-executable instructions further causes the computational system to control the motion sensor system to measure the motion parameters. For example, a respiratory belt or a camera system may be used to directly measure the motion of the subject. In other examples there may be fiducial markers which may be used to optically measure the position of the subject accurately or if there are MRI fiducial markers, may be used to measure the position of the subject in the magnetic resonance image itself.

In another embodiment, execution of the machine-executable instructions further causes the computational system to reconstruct an intermediate image from the subsequent k-space data. Execution of the machine-executable instructions further causes the computational system to calculate a registration between the intermediate image and the initial magnetic resonance image.

Execution of the machine-executable instructions further causes the computational system to calculate the motion parameters from the registration. This embodiment may be beneficial because an external system or motion sensor is not needed to determine the motion parameters. This may also enable a very accurate determination of where the subsequent region of interest is relative to the first region of interest. This may provide for more accurate estimated $B_0$ field calculations In another embodiment the estimated $B_0$ field map is calculated at least partially using an analytical model to calculate a spatial transformation of the estimated $B_0$ field mapping using the motion parameters. For example, if the $B_0$ field mapping is calculated directly from the initial magnetic resonance image then an analytical model can be used to transform the location of the $B_0$ field after the subject has moved.

In another embodiment the estimated $B_0$ field is calculated at least partially by inputting the initial magnetic resonance image and/or the estimated $B_0$ field mapping and the motion parameters into a trained neural network. In this example the trained neural network may be used to predict or estimate the $B_0$ field maps and/or residual $B_0$ field maps using the motion parameters.

In another embodiment, the estimated $B_0$ field is calculated at least partially by inputting the estimated $B_0$ field mapping and the motion parameters into a trained artificial intelligence algorithm. Likewise, in this embodiment, the values of the estimated $B_0$ field mapping may be improved using the trained artificial intelligence algorithm.

In another embodiment, the estimated $B_0$ field is calculated at least partially by inputting the motion parameters into a trained support vector machine. The support vector machine may be trained or programmed to perform this transformation of the motion parameters into estimated $B_0$ field maps.

In another embodiment the memory further contains a system model configured for outputting time dependent data descriptive of electromagnetic properties of the magnetic resonance imaging system in response to inputting the one of the set of second pulse sequence commands. Execution of the machine-executable instructions further causes the computational system to calculate the time dependent data by inputting the subsequent pulse sequence commands into the system model. The corrected magnetic resonance image is reconstructed from the subsequent k-space data, the estimated $B_0$ field mapping, and the time dependent data.

There are a variety of parameters which affect the quality of the magnetic resonance imaging reconstruction that may be calculated or modeled in advance. The time and temperature dependent data is electromagnetic data that is derived from such quantities. The time/temperature dependent data may be descriptive of any one of the following: the $B_0$ field changes, eddy currents within entire portions of the magnetic resonance imaging system, transmit RF field amplitude and inhomogeneity, gradient magnetic field amplitude and nonlinearities, changes in receive coil sensitivities, motion dependent $B_0$ inhomogeneities, concomitant magnetic field corrections, and combinations thereof.

In another embodiment, one of the second pulse sequence commands is configured to acquire the subsequent k-space data according to an echo planar imaging magnetic resonance imaging protocol.

In another embodiment the second pulse sequence commands are configured to acquire the subsequent k-space data according to a multiband magnetic resonance imaging protocol. Both the echo planar imaging and the multiband magnetic resonance imaging may benefit from having shimming and better estimation of the residual $B_0$ inhomogeneities.

In another embodiment the second pulse sequence commands are configured to acquire the subsequent k-space data with a spiral k-space sampling pattern.

In another embodiment the second pulse sequence commands are configured to acquire the subsequent k-space data with a non-Cartesian sampling pattern.

It should be noted though that the embodiments may be beneficial to all k-space sampling patterns or trajectories.

In another embodiment, the $B_0$ field estimation module is implemented as a $B_0$ modeling neural network. The $B_0$ modeling neural network may for example be a neural network such as a convolutional neural network that has been trained to generate an estimate of the $B_0$ field in response to receiving one or more magnetic resonance images. The $B_0$ modeling neural network may for example be trained by measuring magnetic resonance images and then before or afterwards performing another magnetic resonance image to measure a $B_0$ map. The training of the $B_0$ modeling neural network will therefore be a straight forward backpropagation or deep learning algorithm.

In another embodiment the $B_0$ field estimation module is implemented as a machine learning system.

In another embodiment the $B_0$ field estimation module is implemented as a $B_0$ modeling random forest regression system.

In another embodiment the $B_0$ field estimation module is implemented as a $B_0$ support vector machine learning system.

In another embodiment the $B_0$ field estimation module is implemented as a template-based $B_0$ magnetic field predictor system. Template-based systems have been demonstrated to be able to generate $B_0$ magnetic field maps accurately.

In another aspect the invention provides for a computer program comprising machine-executable instructions for execution by a computational system for controlling a medical system. Execution of the machine-executable instructions causes the computational system to receive an initial magnetic resonance image descriptive of a first region of interest of a subject. The initial magnetic resonance image comprises a magnitude component.

Execution of the machine-executable instructions further causes the computational system to perform an iteration of the following at least once: firstly, this is to receive subsequent k-space data descriptive of a subsequent region of interest of the subject. The subsequent region of interest at least partially overlaps the first region of interest.

Execution of the machine-executable instructions further causes the computational system to perform iteratively the calculation of an estimated $B_0$ field mapping for the subsequent region of interest from the initial magnetic resonance image. Execution of the machine-executable instructions further causes the computational system to perform an iteration of the following at least once which is to reconstruct a corrected magnetic resonance image from the subsequent k-space data and the estimated $B_0$ field mapping.

In another aspect, the invention provides for a method of medical imaging. The method comprises receiving an initial magnetic resonance image descriptive of a first region of interest of the subject. The initial magnetic resonance image comprises a magnitude component. Execution of the machine-executable instructions further causes the computational system to perform an iteration of the following at least once: the first step in the iteration is to receive subsequent k-space data descriptive of a subsequent region of interest of the subject.

The subsequent region of interest at least partially overlaps the first region of interest. The next step of the iteration is to calculate an estimated $B_0$ field mapping for the subsequent region of interest from the initial magnetic resonance image by using a $B_0$ field estimation module. The next step of the iteration is to reconstruct a corrected magnetic resonance image from the subsequent k-space data and the estimated $B_0$ field mapping.

The magnetic resonance imaging system of the invention is configured to arrange for reconstruction of the set of magnetic resonance images from the echo signals in that reconstruction software is installed in the magnetic resonance examination system's computational system or in that the computational system has access to a remote reconstruction facility. The reconstruction software may be installed on a remote server, e.g. in the healthcare institution of even accessible to a data-network in that the reconstruction software may be available in 'the cloud', In these remote configurations the computational system is equipped with functionality to arrange for reconstruction of the set of magnetic resonance images at the remotely located reconstruction function. Moreover, reconstruction of the magnetic resonance image may be done by way of machine learning, for example by a trained neural network that may be incorporated ion the computational system or may be accessible from a remote location.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan. Magnetic resonance data is an example of tomographic medical image data.

A Magnetic Resonance Imaging (MRI) image, MR image, or magnetic resonance imaging data is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
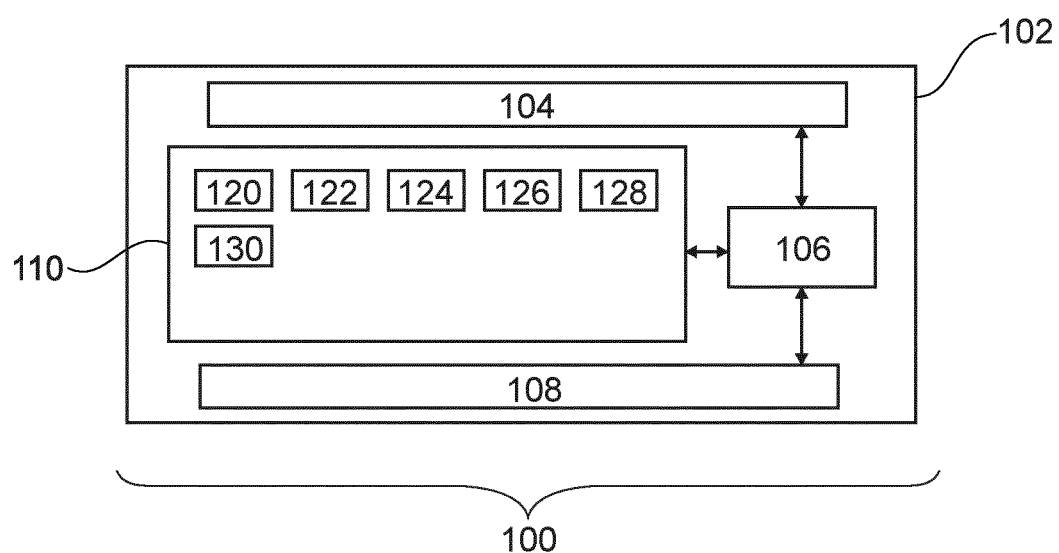
FIG. 1 illustrates an example of a medical system.

FIG. 1 illustrates an example of a medical system 100. The medical system 100 in FIG. 1 is depicted as comprising a computer 102. The computer has an optional hardware interface 104 that may for example enable the computer 102 to communicate or control other components of the medical system 100. The computer 102 is shown as comprising a computational system 106. The computational system 106 may be implemented as a processor or multiple processors and may also be distributed in multiple locations. The computational system 106 may also be a field programmable gate array or other system capable of performing computations. The computer 102 is further shown as comprising an optional user interface 108. The user interface 108 may enable an operator to control the operation and function of the computer 102 and the medical system 100. The computer 102 is further shown as comprising a memory 110. The memory 110 is intended to represent different types of memory 110 that may be accessible to the computational system 106. The computational system 106 is shown as being in communication with the hardware interface 104, the user interface 108, and the memory 110.

The medical system 100 may take different forms in different examples. In one example the medical system 100 may be a remote server or a cloud computing component. In other examples the medical system 100 may be a workstation computer used by a physician or other medical professional. In other examples the medical system 100 may be integrated into the control system of a medical system 100 that controls a magnetic resonance imaging system.

The memory 110 is shown as containing machine-executable instructions 120. The machine-executable instructions 120 enable the computational system 106 to provide and perform various computational tasks. For example, this may include basic data processing, image processing, and medical image reconstruction tasks. The memory 110 is shown as containing an initial magnetic resonance image 122 that was received. It could have for example been received by a data carrier or it may have been received via a network or internet connection. The memory 110 is further shown as containing subsequent k-space data 124. The initial magnetic resonance image is acquired for a first region of interest of the subject. The subsequent k-space data is descriptive of a subsequent region of interest of the subject. In this particular example, the subsequent region of interest is within the first region of interest and has a volume that is less than or equal to the first region of interest. In other examples, the subsequent region of interest and the first region of interest may only be at least partially overlapping.

The memory 110 is further shown as containing a $B_0$ field estimation module 126 that is configured for taking at least magnitude component of a magnetic resonance image as input. In response it outputs an estimated $B_0$ field mapping 128 for the subsequent k-space data 124. The memory 110 is further shown as a corrected magnetic resonance image 130 that was reconstructed from the subsequent k-space data 124 using the estimated $B_0$ field mapping 128. The estimated $B_0$ field mapping 128 could for example be used for correcting for $B_0$ inhomogeneities when the subsequent k-space data 124 was acquired.

Figure 2:
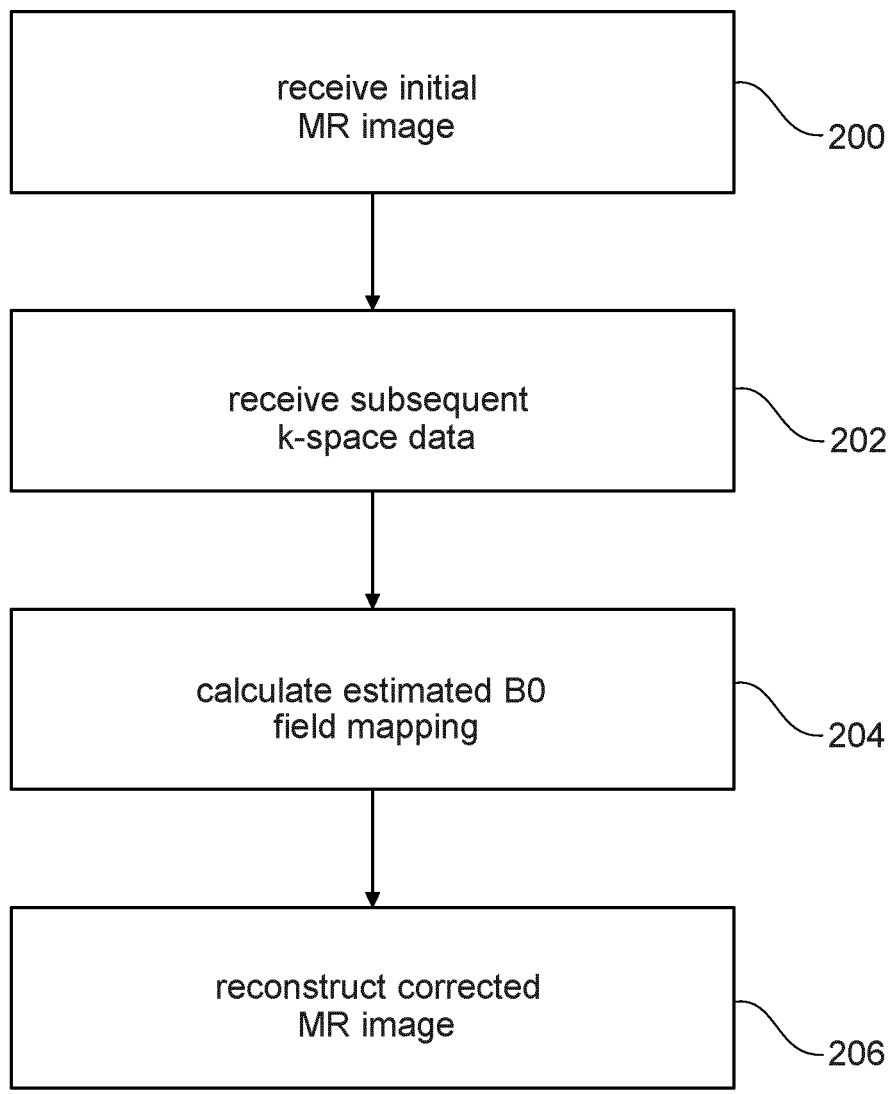
FIG. 2 shows a flow chart which illustrates a method of operating the medical system of FIG. 1.

FIG. 2 shows a flowchart which illustrates a method of operating the medical system 100 of FIG. 1. First, in step 200, the initial magnetic resonance image 122 is received. The initial magnetic resonance image 122 is descriptive of a first region of interest of a subject. The initial magnetic resonance image is a magnitude image. Next, the method proceeds to step 202. In step 202 the subsequent k-space data 124 is received. Next, in step 204, an estimated $B_0$ field mapping 128 is calculated by inputting the initial magnetic resonance image 122 into the $B_0$ field estimation module 126. Then, in step 206, the corrected magnetic resonance image 130 is calculated using the subsequent k-space data 124 and the estimated $B_0$ field mapping 128.

Figure 3:
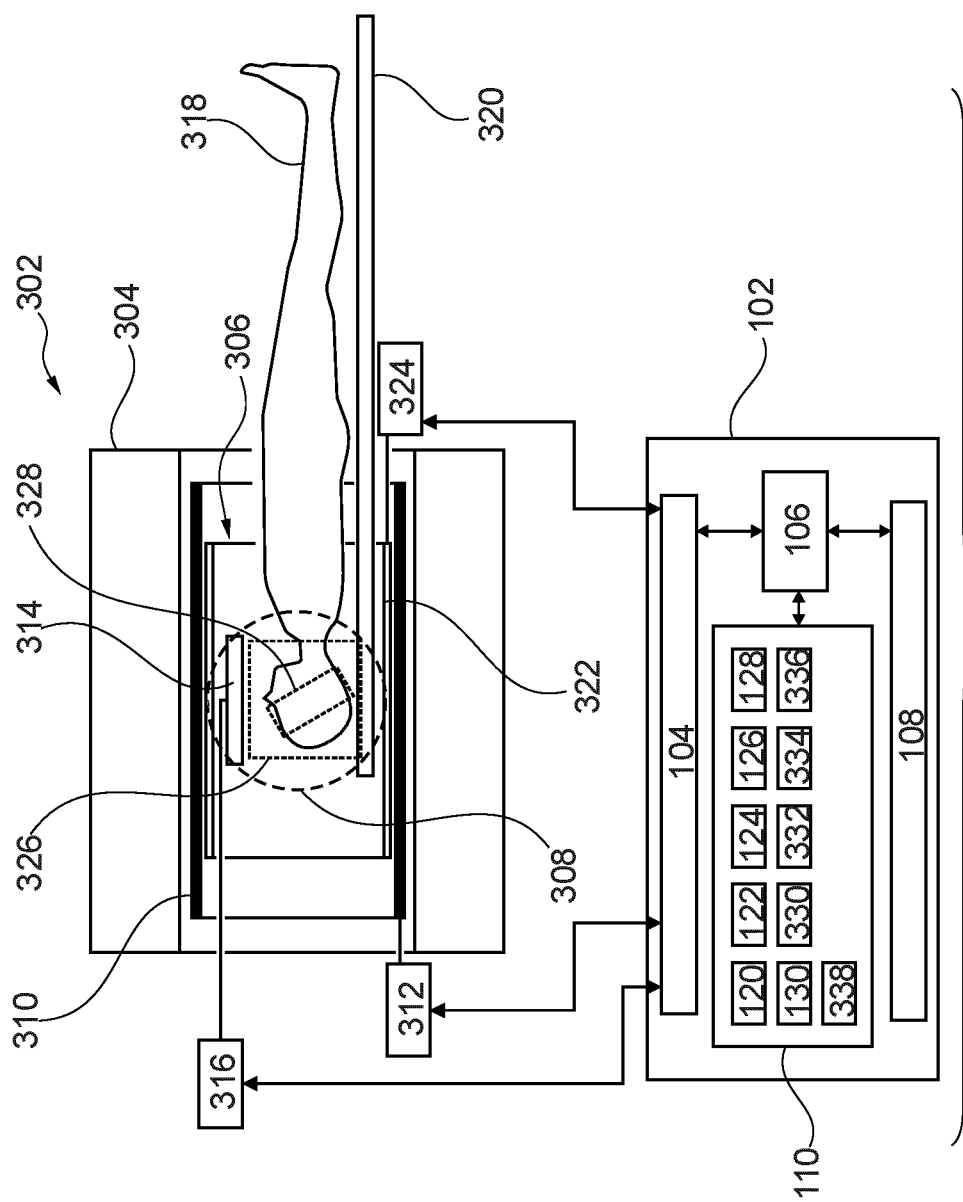
FIG. 3 illustrates a further example of a medical system.

FIG. 3 illustrates a further example of the medical system 300. The medical system 300 is similar to the medical system 100 in FIG. 1 except it additionally comprises a magnetic resonance imaging system 302.

The magnetic resonance imaging system 302 comprises a magnet 304. The magnet 304 may also be referred to as the main magnet. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A subject 318 is shown as being supported by a subject support 320 such that at least a portion of the subject 318 is within the imaging zone 308. Within the bore 306 of the magnet 304 is also visible a $B_0$ magnetic field shim coil 322 that is connected to a $B_0$ magnetic field shim power supply 324. The hardware interface 104 may be used to control and dynamically change the shimming of the main magnetic field of the magnet 304.

Within the imaging zone 308 is visible a first region of interest 326. It can be seen as encompassing almost the entire head region of the subject 318. Because it encompasses and images the entire head region it could provide a very good estimate of the $B_0$ magnetic field inhomogeneities caused by placing the subject 318 within the imaging zone 308. Also, within the imaging zone 308 is visible a subsequent region of interest 328. This region is seen as being very closely around just a portion of the subject's 318 head. This may be used for providing clinical or more detailed magnetic resonance images. However, because only a small region of the head is imaged, it would not accurately produce information about the $B_0$ inhomogeneities. The regions of the subject 318 outside of the subsequent region of interest 328 would also have the effect of distorting the $B_0$ or main magnetic field.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316, the magnetic field gradient coil power supply 312, and the gradient controller 312 are shown as being connected to the hardware interface 106 of a computer system 102.

The memory 110 is further shown as containing first pulse sequence commands 330. The memory 110 is further shown as containing initial k-space data 332 that was acquired from the first region of interest 326 by controlling the magnetic resonance imaging system 302 with the first pulse sequence commands 330. The memory 110 is further shown as containing a set of second pulse sequence commands 334. These represent a variety of different magnetic resonance imaging protocols to which k-space data can be acquired. The memory 110 is further shown as containing one or a selection of the second pulse sequence commands 336. This is just one of the set 334. The memory 110 is further shown as containing subsequent k-space data 338 that was acquired for the subsequent region of interest 328 by controlling the magnetic resonance imaging system 302 with the one 336 of the second pulse sequence commands. The process may be repeated for different selections of the set of second pulse sequence commands 334. This may also involve that for each acquisition there is a different subsequent region of interest 328. This for example may enable a very flexible system of estimating the $B_0$ field mapping 128 for a variety of different acquisitions.

Figure 4:
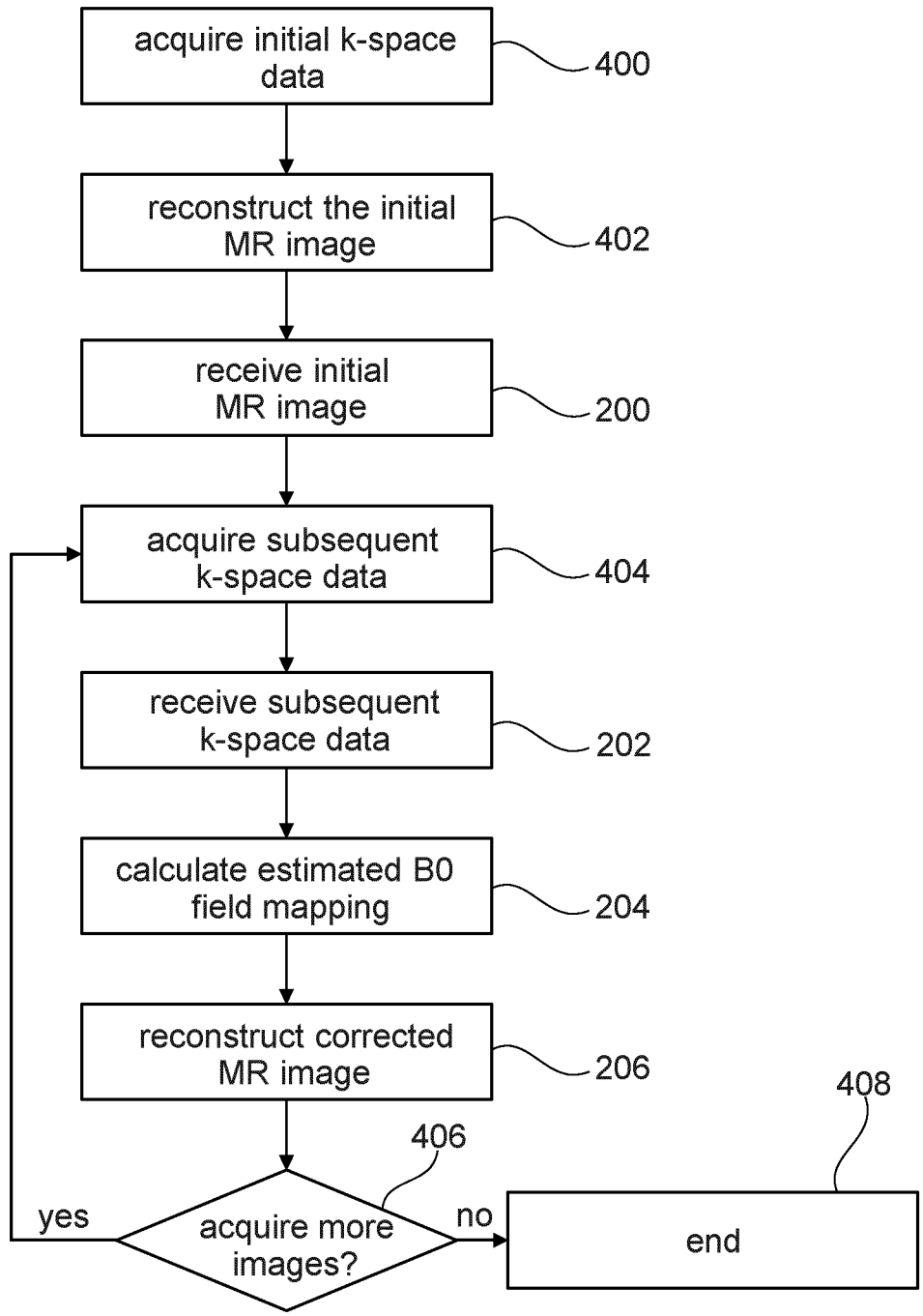
FIG. 4 shows a flow chart which illustrates a method of operating the medical system of FIG. 3.

FIG. 4 shows a flowchart which illustrates a method of operating the medical system 300 of FIG. 3. First, in step 400, the magnetic resonance imaging system 302 is controlled with the first pulse sequence commands 330 to acquire the initial k-space data 332. Next, in step 402, the initial magnetic resonance image 122 is reconstructed from the initial k-space data 332. The method then proceeds to step 200 of FIG. 2. After step 200, step 404 is performed. In step 404 the magnetic resonance imaging system 302 is controlled with the one 336 of the second pulse sequence commands to acquire the subsequent k-space data 338. The method then proceeds through steps 202, 204, and 206 of FIG. 2. Step 406 is a decision box and the question is are there more images to acquire. If the answer is yes then the method proceeds back to step 404. If the answer is no the method proceeds to step 408 where the method ends.

Figure 5:
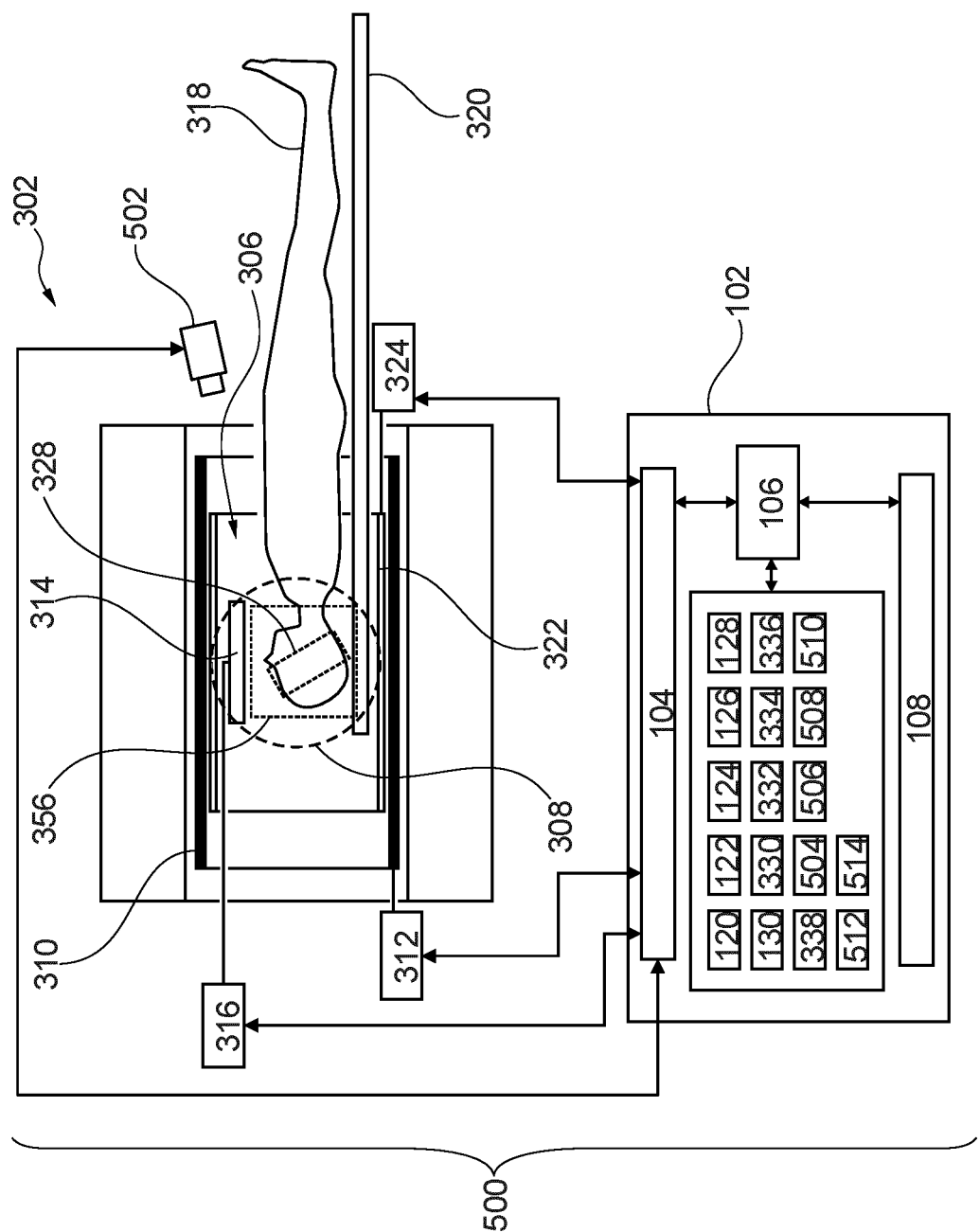
FIG. 5 illustrates a further example of a medical system.

FIG. 5 illustrates a further example of a medical system 500. The medical system 500 illustrated in FIG. 5 is similar to the medical system 300 in FIG. 3 except that it additionally comprises a camera system 502. The camera system 502 may for example be used for directly measuring motion parameters descriptive of motion of the subject 318 during acquisition of the subsequent k-space data 338. The memory 110 is further shown as containing updated shim settings 504. These updated $B_0$ shim settings may be configured to reduce the $B_0$ inhomogeneity by controlling the $B_0$ magnetic field shim power supply 324. The camera system 502 is a motion sensor system. The memory 110 is further shown as containing an intermediate image 508 that has been reconstructed from the subsequent k-space data 338 possibly without the $B_0$ corrections and also without motion corrections. The memory 110 is further shown as containing the image registration 510 between the intermediate image 508 and the initial magnetic resonance image 112. This may be used to determine motion parameters 506 which are also shown as being stored in the memory 110. The camera system 502 can also measure the motion parameters 506. In some cases, both the camera 502 and the image registration 510 may both be used for deriving or calculating the motion parameters 506.

The memory 110 is further shown as optionally containing a system model 512. The system model 512 contains a model of the magnetic resonance imaging system 302 in terms of its electromagnetic properties as a function of time in response to the pulse sequence commands. This can be used for such things as modeling the $B_0$ inhomogeneities caused by eddy currents, the temperature dependent gradient magnetic field nonlinearities, other time dependent gradient magnetic field nonlinearities, changes in magnetic resonance coil sensitivities, motion dependent $B_1$ inhomogeneities, static magnetic gradient field nonlinearities and concomitant magnetic field corrections. The memory 110 is further shown as containing time dependent data 514 output by the system model 512 in response to inputting the one 336 of the second pulse sequence commands. This time dependent data 514 may be used in improving the reconstruction of the corrected magnetic resonance image 130.

Figure 6:
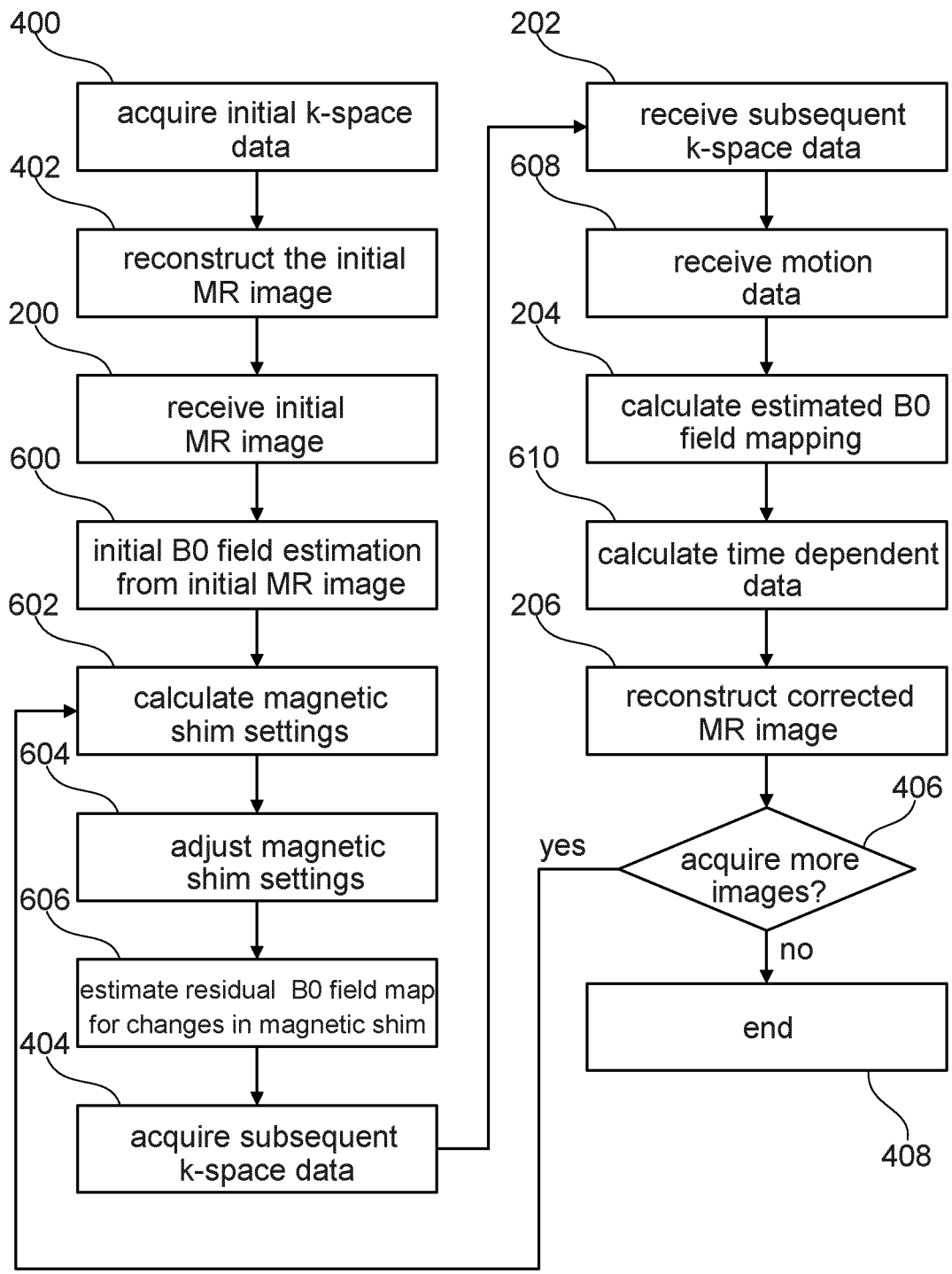
FIG. 6 shows a flow chart which illustrates a method of operating the medical system of FIG. 5.

FIG. 6 shows a flowchart which illustrates a method of operating the medical system 500 of FIG. 5. Steps 400, 402, and 200, as is illustrated in FIG. 4, are performed first. Next, step 600 is optionally performed. In step 600 an initial $B_0$ field mapping is estimated from the initial image. For example, if it is desired to shim the $B_0$ magnetic field the initial $B_0$ field mapping can be used for the first pass of the algorithm. Next, the method proceeds to step 602. Step 602 is also optional. In step 602 the updated $B_0$ shim settings are calculated and configured to reduce $B_0$ inhomogeneity using either the estimated $B_0$ field mapping or the initial $B_0$ field mapping.

Next, optional step 604 is performed. In step 604 the $B_0$ magnetic field is shimmed by controlling the adjustable $B_0$ magnetic field shim with the updated $B_0$ shim settings. After step 606 the method proceeds to step 404 of FIG. 4. Then step 202, as was illustrated in FIG. 4, is also performed. The method then proceeds to step 608. Step 608 is also optional. In step 608 motion parameters 506 are received. The motion parameters are descriptive of motion of the subject 318 during or after acquisition of the subsequent k-space data 338. After step 608, step 204 as was previously described in FIG. 4, is performed. After step 204, optional step 610 is performed. In step 610 the time dependent data 514 is calculated by inputting the one 336 of the second pulse sequence commands into the system model 512. After step 610, step 206 as was described in FIG. 4, is performed. During the reconstruction of the corrected magnetic resonance image 130 the time dependent data 514 may be used if it is present.

Figure 7:
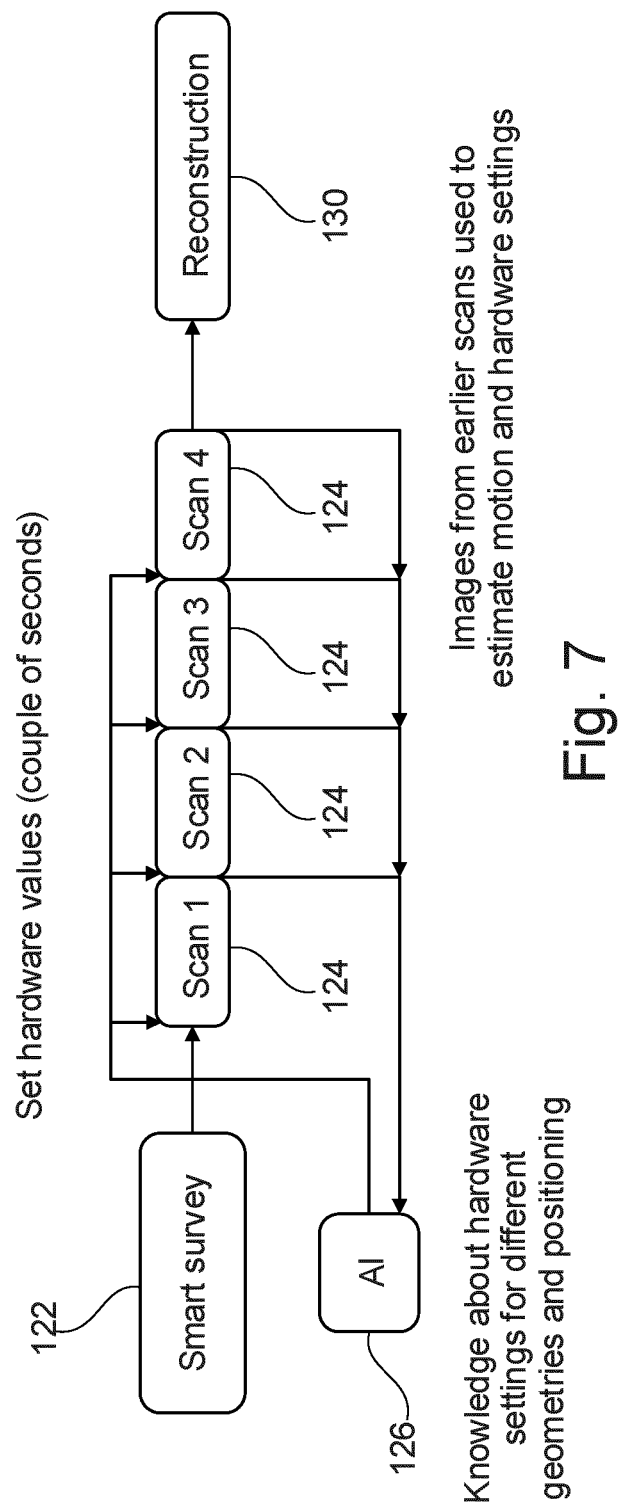
FIG. 7 illustrates a method of medical imaging.

FIG. 7 illustrates one method of medical imaging. In this example a so-called smart survey which corresponds to the initial magnetic resonance image 122 is acquired. This incorporates using a survey scan to calculate the $B_0$ magnetic field. An artificial intelligence module which corresponds to the $B_0$ field estimation module 126 is used before each acquisition of the subsequent k-space data 124 to correct and set hardware values such as the shimming of the $B_0$ field. Images from earlier scans 124 may be used to estimate motion and/or hardware settings. At the end the data from the various acquisitions is used for a reconstruction of the corrected magnetic resonance image 130.

Figure 8:
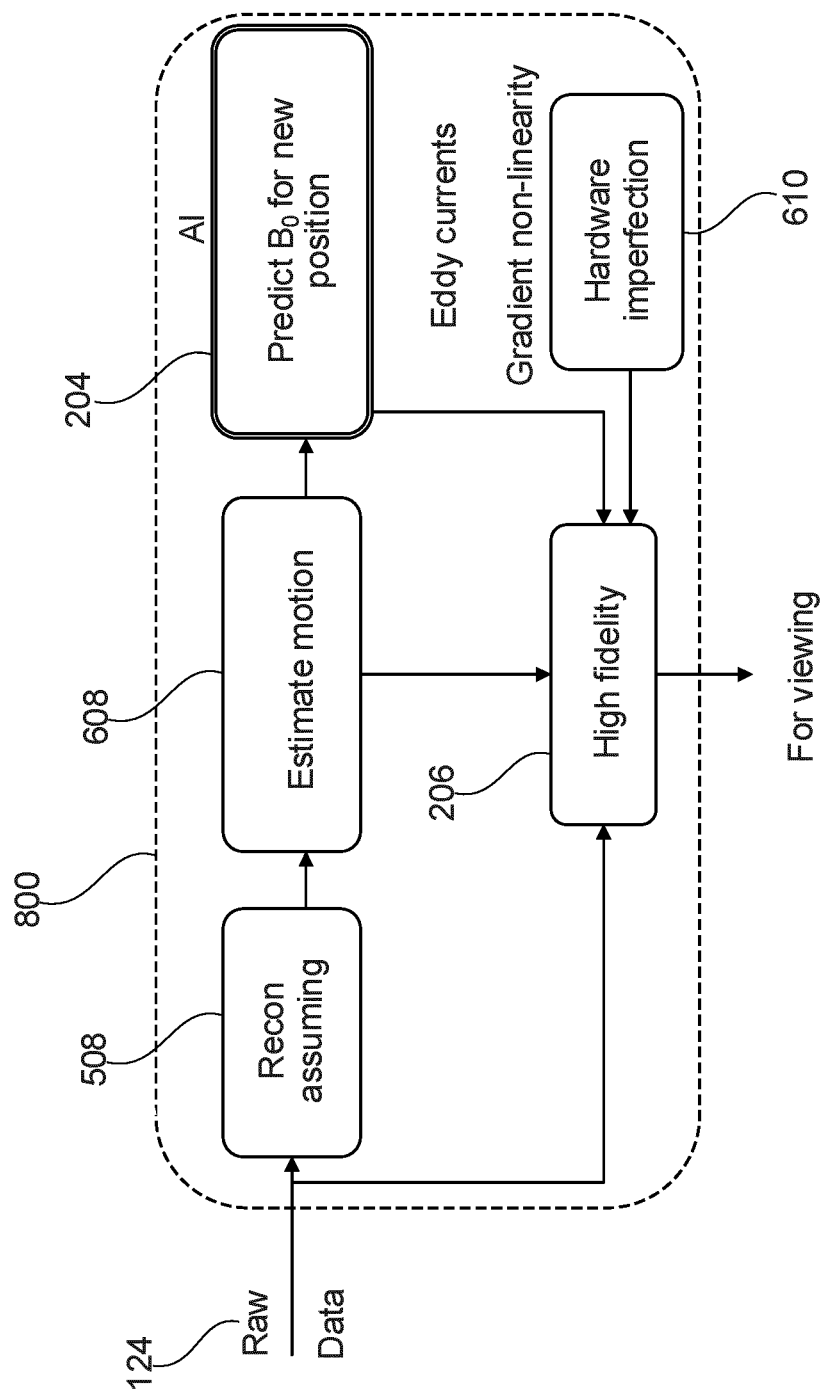
FIG. 8 illustrates an example of an image reconstruction module.

FIG. 8 illustrates an example of an image reconstruction module 800. The raw k-space data or subsequent k-space data 124 is input into it. First there is a reconstruction that reconstructs an intermediate image 508. This intermediate image 508 is reconstructed without motion correction and also possibly without corrections for the $B_0$ inhomogeneities. The next step in the module estimates the motion 608. The motion parameters are received, this may be from an external camera system 502 or it may also be received from an image registration 510. This is then input into the next portion of the module which predicts 204 a new $B_0$ for the new position of the subject. There may also be optionally a system which models the electromagnetic properties of the magnetic resonance imaging system and models hardware imperfections 610. The modeled electromagnetic properties of the magnetic resonance imaging system is the time dependent data 514, which may be calculated by inputting the pulse sequence commands into the system model 512. The module then performs a high-fidelity reconstruction 206 that uses the subsequent k-space data 124, the motion estimation from 608, the new $B_0$ field from 204 and the hardware imperfections 610.

Figure 9:
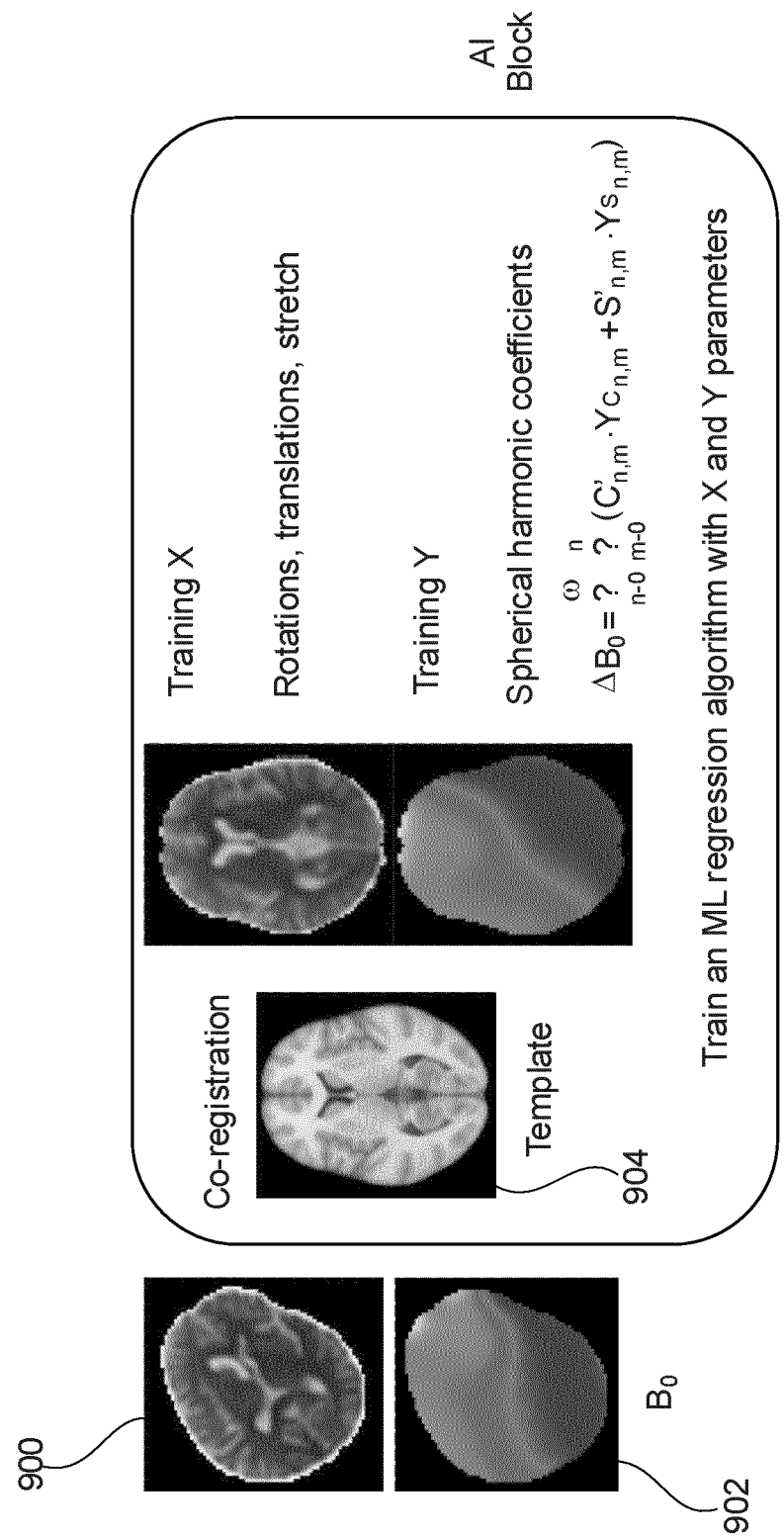
FIG. 9 illustrates a method of training a template-based AI system to calculate $B_0$ inhomogeneity maps.

FIG. 9 illustrates the training of the artificial intelligence block. In this case the artificial intelligence block uses a machine learning algorithm that is trained by using measured images along with measured $B_0$ field inhomogeneities 902 to co-register to a template 904. Parameters involving the transformation of the image 900 are trained as well as transformations for the measured $B_0$ field inhomogeneities 902. The combination of these translations of the image and of the $B_0$ field inhomogeneities 902 can be used to train a machine language regression algorithm with both these parameters. The training for the measured $B_0$ field inhomogeneities 902 is done using co-registration parameters and spherical harmonic coefficients.

Figure 10:
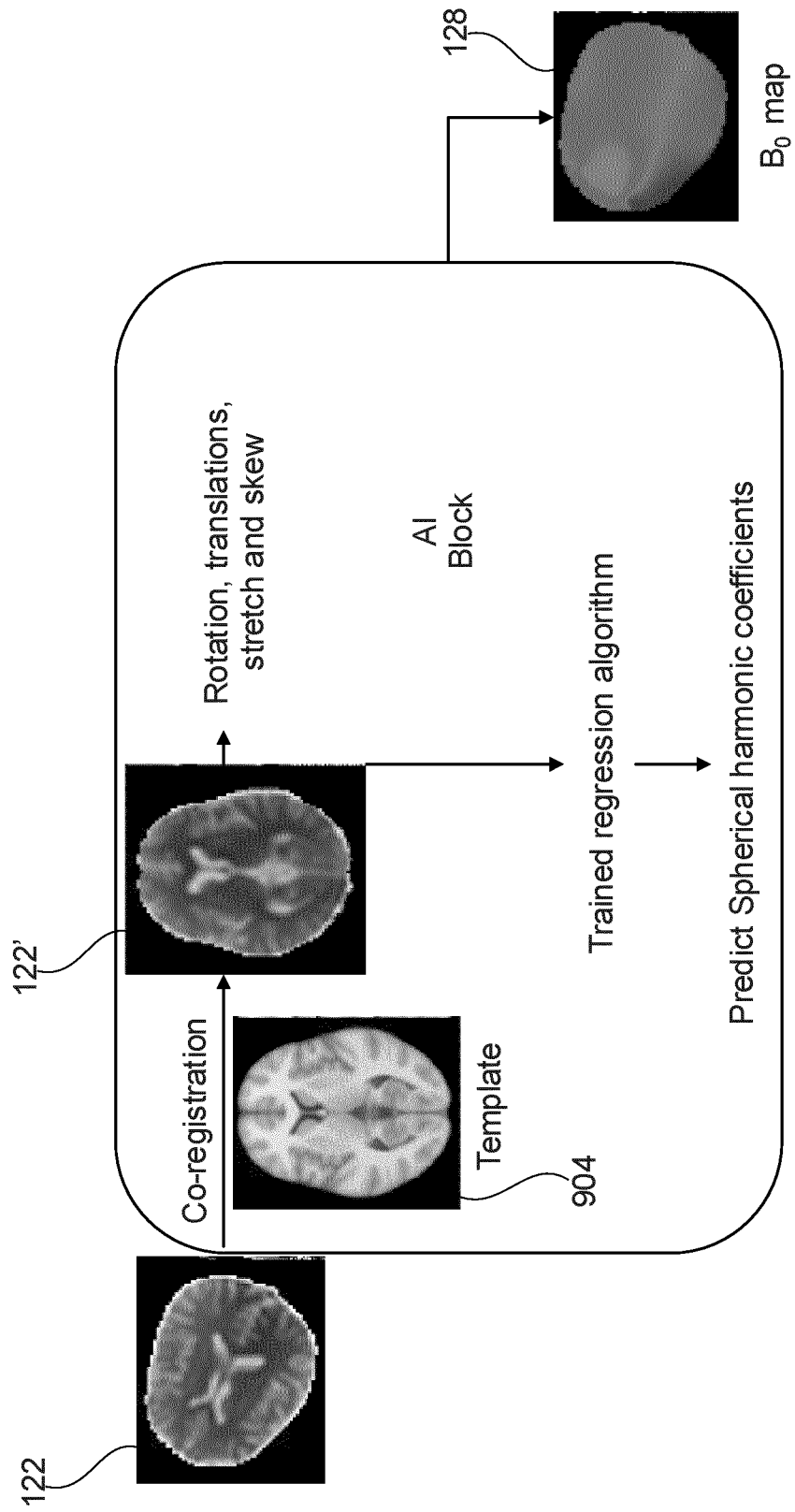
FIG. 10 illustrates the use of the AI system of FIG. 9 to produce a $B_0$ inhomogeneity map.

FIG. 10 illustrates the calculation of the $B_0$ field mapping 128 using the system illustrated in FIG. 9. The initial magnetic resonance image 122 is co-registered to a template 904. This results in a transformed initial magnetic resonance image 122. Inputting these transformations into the artificial intelligence block of FIG. 9 enables prediction of the spherical harmonic coefficients and results in the estimated $B_0$ field mapping 128. The rotations, translations and stretching skew, which were calculated for the initial magnetic resonance image, may be updated with the motion parameters 506 are then used to calculate the correct estimated $B_0$ field mapping.

As was mentioned previously magnetic resonance imaging (MRI) scanners use $B_0$ preparatory scans to improve SNR and also image quality during reconstruction (e.g. reduce image distortion in EPI, MB-SENSE, spirals). However, the preparatory scans can add substantial time to the overall scan duration (up to 10%). Moreover, despite using the $B_0$ prescan, MRI images sometimes suffer from artifacts, ranging anywhere from being subtle to gross image degradation. Typically, motion and respiration combine with scanner hardware limitations and give rise to the artifacts. Occurrence of artifacts necessitates repeat scans, resulting in reduced scanner throughput and reduced patient comfort. Moreover, it also affects measurement confidence through reduced image quality. This is a widespread problem that affects nearly all MRI systems, and across all application areas.

An example image acquisition/reconstruction framework, such as depicted in FIG. 6 or 8, may solve this issue in a comprehensive manner by accounting for the fundamental physics behind the problem over a large class of fast MRI scans (EPI, MB-SENSE, spirals etc.). Examples may also lead to direct scan time reduction by eliminating the $B_0$ preparatory scans needed for MRI exams. AI may be a key enabler in both acquisition and reconstruction stages.

Examples may provide the combined benefits of improved image quality and reduced scan time.

Even in a well calibrated MRI scanner, artifacts affect image quality to varying extents, depending on the scan type and anatomy of interest. The root cause of the artifacts can be subdivided into two major types listed below with their causes:
1. System imperfections (examples given below)
   a. Eddy currents (can be fully modeled both in space and time for all acquisition conditions)
   b. Gradient nonlinearities (completely modeled for all conditions)
2. Human physiology related (examples given below)
   a. Magnetic field inhomogeneity (dependent on region of interest)
   b. Motion, breathing etc. (not easily characterized, but can be measured using tools like imaging)

System imperfections can be fully quantified with calibration scans performed once during installation and their impact is typically mitigated either during acquisition and/or during image reconstruction. However, physiology-induced artifacts are hard to predict. Some sources like magnetic field inhomogeneity are mitigated with preparatory-scans ($B_0$ prescans). But that leads to increased scan time and could lead to significant overheads. However, most attempts try to mitigate artifacts using image processing, or have no solutions at all, requiring a repeat scan. In particular, motion induced artifacts are hard to quantify and correct, especially with dynamic scans which acquire a series of image volumes over time.

One issue which is often neglected, but important to note here is, all the sources of artifacts interact with each other and cannot be corrected using post-processing. For example, in case of brain scans, head motion changes magnetic field inhomogeneity, and also results in varying effects of eddy-currents and gradient nonlinearity. One way to maintain image fidelity under such conditions is to incorporate all the sources of artifacts into a single image reconstruction framework. This has resulted in a plethora of post-processing options, which try to correct different artifacts in a piecemeal manner, with none being able to provide the same image fidelity as accounting for all the causes concurrently during reconstruction.

Examples may address two technical issues. A) Eliminate the need for acquiring $B_0$ prescans using in some examples AI-based predictions. B) Provide true fidelity reconstructions even in case of motion by using the same AI-based prediction strategy to predict residual $B_0$ inhomogeneity after shimming which would be used as input to the reconstruction algorithm.

The $B_0$ prescans that are performed routinely on the scanners before many scans do not directly offer any diagnostic value. But they are currently essential to improve SNR (shimming). They are also used to provide inputs to reconstruction algorithms to improve image quality. However, that comes with an assumption that the patient does not move between the prescan and the main scan. This assumption is often violated in practice, leading to image quality degradation.

Examples may eliminate the need for performing $B_0$ prescans and thus lead to direct scan time reduction. This could save 10% or more in terms of overall scan time. Moreover, this may provide for a way to predict $B_0$ inhomogeneity and thus directly improve image quality for a large class of scans, even in the presence of motion. Thus, examples may provide for a motion-robust, reduced scan time acquisition and reconstruction framework.

Recent studies have highlighted that the $B_0$ inhomogeneity in humans is very similar across subjects, irrespective of the anatomy under consideration. The main variability in $B_0$ inhomogeneity stems from different anatomical shapes and patient positioning inside the scanners. Both these will be captured by the survey scan done (initial magnetic resonance image 122) in every MR examination to aid planning.

Examples may benefit the very widely used fast imaging scans like echo-planar imaging (EPI) and its variants (e.g., MB-SENSE) and also scans with great clinical potential which have not been widely adopted so far because of their vulnerability to artifacts, for example, spiral imaging. Both types of scans typically capture image volumes within a few seconds.

Examples also provide for the implementation of a comprehensive image acquisition/reconstruction framework as is shown in FIGS. 6 and 8. This framework may be used to take into account time dependent data 514 such as eddy currents, gradient nonlinearities and magnetic field inhomogeneity. In examples, the reconstruction framework may include motion-related effects (direct and indirect), but also to reduce scan time by eliminating the need of the preparatory scan performed to measure magnetic field inhomogeneity (by determining the estimated $B_0$ field mapping 128).

One of the hurdles in developing a comprehensive image reconstruction framework including motion is an assumption underlying current image reconstruction techniques. For example, current EPI and spiral image reconstructions perform a preparatory scan (prescan) to measure magnetic field inhomogeneity, but inherently assume that there is no motion between the preparatory scan and the main scan (EPI/spiral) acquisitions. However, this assumption can be violated, especially in a dynamic scan involving multiple volumes where subject motion typically leads to unexpected artifacts. In contrast to the disclosed examples, the currently used frameworks may typically require repeated preparatory scans to measure magnetic field inhomogeneity which is completely infeasible in dynamic scans, as motion occurs continuously (especially in the torso region).

Recent research has shown that in brain scans, one can predict the magnetic field inhomogeneity resulting from motion if the initial magnetic field inhomogeneity distribution is known. While this concept has been used to correct EPI images at the post-processing stage, examples may incorporate this concept directly into the reconstruction framework as disclosed herein. Examples may predict magnetic field inhomogeneity using survey scans using AI and thus eliminate the need of acquiring preparatory scans for measuring magnetic field inhomogeneity.

An example acquisition/reconstruction framework may involve one or more of the following steps:
  a) Perform survey scan for planning (e.g. EPI/spiral volume) (receive 200 initial magnetic resonance image 122)
  b) Predict magnetic field inhomogeneity from survey scans using AI (calculate an estimated $B_0$ field mapping 204 or calculate an initial $B_0$ field mapping 600)
  c) Improve the field homogeneity by setting appropriate shim currents (calculate 602 updated shim settings 504 and shim 604 the $B_0$ magnetic field) and also predict the residual magnetic field inhomogeneity (adjust the estimated $B_0$ field mapping using the change in the $B_0$ shim settings 606). This can be done using simple calculations.
  d) Perform EPI/Spiral dynamic scan (multiple volumes over time, e.g. DTI, fMRI, bolus tracking etc.) (acquire 404 the subsequent k-space data 124)

e) Reconstruct the first image volume in the series with high fidelity using residual magnetic field obtained from step c and with the knowledge of system imperfections. Note that there may be no time gap between prediction at step c and the acquisition of first volume in the time series. (reconstruct 206 a corrected magnetic resonance image 130)

f) For each subsequent image volume
1. Perform low quality reconstruction (reconstruct the intermediate image 508) (with the existing framework and not the proposed one) and use image co-registration (registration 510) to the first volume (first region of interest 326) to estimate motion parameters (translations, rotations, skew and stretch). Alternatively, obtain reliable motion estimates from other sources, e.g. from a camera system 502.
2. Use the motion parameters to predict residual magnetic field inhomogeneity using AI (calculate 128 the estimated $B_0$ field mapping 128 using the $B_0$ field estimation module 126)
3. Use the motion parameters 506 and the predicted residual magnetic field inhomogeneity along with updated system imperfections (to account for motion) in the comprehensive reconstruction framework to obtain high fidelity reconstructions (the corrected magnetic resonance image 130).

Some examples may provide for a $B_0$ prescan prediction (estimated $B_0$ field mapping 128) from survey scan and there by its elimination from actual scanning can be used irrespective of the scanner (field strength and variant), scan type and potentially anatomy as well (although our initial tests have been restricted to brain scans). This directly leads to scan time reduction by pre-scan elimination.

Other examples may provide for incorporating the residual $B_0$ in image reconstruction applies to all the fields strength and variants and a large class of MRI scans, both currently in the field and those being newly developed. e.g. EPI distortion correction, SENSE, MB-SENSE, CSENSE etc., which are all already in the field can benefit from the proposed comprehensive reconstruction framework, as long as the acquisition volume can be acquired in a few second (<10 s), which they typically do.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 computer
104 hardware interface
106 computational system
108 user interface
110 memory
120 machine executable instructions
122 initial magnetic resonance image
124 subsequent k-space data
126 $B_0$ field estimation module
128 estimated $B_0$ field mapping
130 corrected magnetic resonance image
200 receive an initial magnetic resonance image descriptive of a first region of interest of a subject, wherein the initial magnetic resonance image is a magnitude image
202 receive subsequent k-space data descriptive of a subsequent region of interest of the subject, wherein the subsequent region of interest is within the first region of interest
204 calculate an estimated $B_0$ field mapping for the subsequent region of interest from the initial magnetic resonance image by inputting the initial magnetic resonance image into the $B_0$ field estimation module
206 reconstruct a corrected magnetic resonance image from the subsequent k-space data and the estimated $B_0$ field mapping
300 medical system
302 magnetic resonance imaging system
304 main magnet
306 bore of magnet
308 imaging zone
310 magnetic field gradient coils
312 magnetic field gradient coil power supply
314 radio-frequency coil
316 transceiver
318 subject
320 subject support
322 $B_0$ magnetic field shim coils
324 $B_0$ magnetic field shim power supply
326 first region of interest
328 subsequent region of interest
330 first pulse sequence commands
332 initial k-space data
334 set of second pulse sequence commands
336 one of the second pulse sequence commands
338 subsequent k-space data
400 control the magnetic resonance imaging system with the first pulse sequence commands to acquire the initial k-space data
402 reconstruct the initial magnetic resonance image from the initial k-space data
404 control the magnetic resonance imaging system with one of the set of second pulse sequence commands to acquire the subsequent k-space data for each iteration
500 medical system
502 camera system
504 updated shim settings
506 motion parameters
508 intermediate image
510 registration
512 system model
514 time dependent data
600 calculate an initial $B_0$ field mapping from the initial magnetic resonance image 602 calculate updated $B_0$ shim settings configured to reduce $B_0$ inhomogeneity using the estimated $B_0$ field mapping 604 shim the $B_0$ magnetic field by controlling the adjustable $B_0$ magnetic field shim with the updated $B_0$ shim settings 606 use the change in $B_0$ shim settings to adjust the estimated $B_0$ field mapping 608 receive motion parameters descriptive of motion of the subject during or after acquisition of subsequent k-space data 610 calculate time dependent data 800 reconstruction module 900 measured image 902 measured $B_0$ field inhomogeneities 904 template

The invention claimed is:

1. A medical system comprising:
a memory configured to store machine executable instructions and a $B_0$ field estimation module configured to output an estimated $B_0$ field mapping in response to receiving at least a magnitude component of an initial magnetic resonance image as input; and
a computational system configured to control the medical system, wherein execution of the machine executable instructions causes the computational system to receive the initial magnetic resonance image, wherein the initial magnetic resonance image is descriptive of a first region of interest of a subject;
wherein execution of the machine executable instructions further causes the computational system to:
receive subsequent k-space data descriptive of a subsequent different region of interest of the subject, wherein the subsequent region of interest at least partially overlaps with the first region of interest and wherein the subsequent k-space data includes motion parameters descriptive of motion of the subject during the acquisition of the subsequent k-space data;
calculate the estimated $B_0$ field mapping for the subsequent region of interest from the initial magnetic resonance image by inputting the initial magnetic resonance image into the $B_0$ field estimation module; and
reconstruct a corrected magnetic resonance image (130) from the subsequent k-space data and the estimated $B_0$ field mapping.

2. The medical system of claim 1, wherein the medical system further comprises a magnetic resonance imaging system configured to acquire k-space data from an imaging zone, wherein the memory further contains first pulse sequence commands configured to acquire initial k-space data from the first region of interest, wherein the memory further contains a set of second pulse sequence commands each configured to acquire the subsequent k-space data from the subsequent region of interest, wherein execution of the machine executable instructions further causes the computational system to:
control the magnetic resonance imaging system with the first pulse sequence commands to acquire the initial k-space data; and
reconstruct the initial magnetic resonance image from the initial k-space data; and
control the magnetic resonance imaging system with one of the set of second pulse sequence commands to acquire the subsequent k-space data for each iteration in that each iteration includes reconstructing a corrected magnetic resonance image from the subsequent k-space data and the estimated $B_0$ field mapping.

3. The medical system of claim 2, wherein the magnetic resonance imaging system comprises a main magnet configured to generate a $B_0$ magnetic field in the imaging zone, wherein the magnetic resonance imaging system further comprises an adjustable $B_0$ magnetic field shim configured to shim the $B_0$ magnetic field in the imaging zone,
wherein execution of the machine executable instructions further causes the computational system to perform the following before each acquisition of the subsequent k-space data:
calculate updated $B_0$ shim settings configured to reduce $B_0$ inhomogeneity using the estimated $B_0$ field mapping; and
shim the $B_0$ magnetic field by controlling the adjustable $B_0$ magnetic field shim with the updated $B_0$ shim settings.

4. The medical system of claim 3, wherein the estimated $B_0$ field mapping is calculated at least partially using the updated $B_0$ shim settings.

5. The medical system of claim 3, wherein execution of the machine executable instructions further causes the computational system to perform the following for the acquisition of the subsequent k-space data: receive motion parameters descriptive of motion of the subject during acquisition of subsequent k-space data; wherein the estimated $B_0$ field is calculated at least partially using the motion parameters.

6. The medical system of claim 5, wherein the medical system further comprises a motion sensor system configured for at least partially measuring the motion parameters, wherein execution of the machine executable instructions further causes the computational system to control the motion sensor system to measure the motion parameters.

7. The medical system of claim 5, wherein execution of the machine executable instructions further causes the computational system to:
reconstruct an intermediate image from the subsequent k-space data;
calculate a registration between the intermediate image and the initial magnetic resonance image; and
calculate the motion parameters from the registration.

8. The medical system of claim 5, wherein the estimated $B_0$ field mapping is calculated at least partially by at least one of the following:
using an analytical model to calculate a spatial transformation of the estimated $B_0$ field mapping using the motion parameters; or
inputting the initial magnetic resonance image and the motion parameters into a trained neural network.

9. The medical system of claim 2, wherein the memory further contains a system model configured to output time dependent data descriptive of electromagnetic properties of the magnetic resonance imaging system in response to inputting the one of the set of second pulse sequence commands, wherein execution of the machine executable instructions further causes the computational system to calculate the time dependent data by inputting the subsequent pulse sequence commands into the system model, wherein the corrected magnetic resonance image is reconstructed from the subsequent k-space data, the estimated $B_0$ field mapping, and the time dependent data.

10. The medical system of claim 9, wherein the time dependent data is descriptive of at least one of the following: $B_0$ inhomogeneities caused by eddy currents, temperature dependent gradient magnetic field nonlinearities, time dependent gradient magnetic field nonlinearities, changes in magnetic resonance coil sensitivities, motion dependent $B_1$ inhomogeneities, static magnetic gradient field nonlinearities, or concomitant magnetic field corrections.

11. The medical system of claim 2, wherein the one of the second pulse sequence commands is configured to acquire the subsequent k-spaced data according to at least one of the following:
   according to an Echo Planar Imaging magnetic resonance imaging protocol;
   according to a Multiband magnetic resonance imaging protocol;
   with a spiral k-space sampling pattern; or
   with a non-Cartesian sampling pattern.

12. The medical system of claim 1, wherein the $B_0$ field estimation module is implemented by at least one of the following:
   a $B_0$ modeling machine learning system;
   a $B_0$ modeling neural network;
   a $B_0$ modeling random forest regression system;
   a $B_0$ support vector machine learning system; or
   a template based $B_0$ magnetic field predictor system.

13. The medical system of claim 1, wherein
   the subsequent region of interest is within the first region of interest, wherein the subsequent region of interest has a volume less than or equal to the first region of interest; or
   the subsequent region of interest has a volume greater than the first region of interest.

14. A computer program comprising machine executable instructions stored in non-transitory computer readable medium for execution by a computational system to control a medical system, wherein execution of the machine executable instructions causes the computational system to: receive an initial magnetic resonance image descriptive of a first region of interest of a subject, wherein the initial magnetic resonance image comprises a magnitude component;
   wherein execution of the machine executable instructions further causes the computational system to:
   receive subsequent k-space data descriptive of a subsequent different region of interest of the subject, wherein the subsequent region of interest at least partially overlaps the first region of interest and wherein the subsequent k-space data includes motion parameters descriptive of motion of the subject during the acquisition of the subsequent k-space data;
   calculate an estimated $B_0$ field mapping for the subsequent region of interest from the initial magnetic resonance image by inputting the initial magnetic resonance image into the $B_0$ field estimation module, wherein the $B_0$ field estimation module is configured to output the estimated $B_0$ field mapping in response to receiving at least the magnitude component of the initial magnetic resonance image; and
   reconstruct a corrected magnetic resonance image from the subsequent k-space data and the estimated $B_0$ field mapping.

15. A method of medical imaging, wherein the method comprises receiving an initial magnetic resonance image descriptive of a first region of interest of a subject, wherein the initial magnetic resonance image comprises a magnitude component;
   wherein the method comprises:
   receiving subsequent k-space data descriptive of a subsequent different region of interest of the subject, wherein the subsequent region at least partially overlaps with the first region of interest and wherein the subsequent k-space data includes motion parameters descriptive of motion of the subject during the acquisition of the subsequent k-space data;
   calculating an estimated $B_0$ field mapping for the subsequent region of interest from the initial magnetic resonance image by inputting the initial magnetic resonance image into a $B_0$ field estimation module, wherein the $B_0$ field estimation module configured for outputting the estimated $B_0$ field mapping in response to receiving at least the magnitude component of the initial magnetic resonance image as input; and
   reconstructing a corrected magnetic resonance image from the subsequent k-space data and the estimated $B_0$ field mapping.

16. The method of claim 15, further comprising:
   before each acquisition of the subsequent k-space data:
   calculate updated B0 shim settings configured to reduce B0 inhomogeneity using the estimated B0 field mapping; and
   shim the B0 magnetic field by controlling the adjustable B0 magnetic field shim with the updated B0 shim settings.

17. The method of claim 16, wherein the estimated B0 field mapping is calculated at least partially using the updated B0 shim settings.

18. The method of claim 16, further comprising: receiving motion parameters descriptive of motion of the subject during acquisition of subsequent k-space data; wherein the estimated B0 field is calculated at least partially using the motion parameters.

19. The method of claim 18, further comprising: measuring the motion parameters, wherein execution of the machine executable instructions further causes the computational system to control the motion sensor system to measure the motion parameters.

20. The method of claim 18, further comprising:
   reconstructing an intermediate image from the subsequent k-space data;
   calculating a registration between the intermediate image and the initial magnetic resonance image; and
   calculating the motion parameters from the registration.

* * * * *